(12) United States Patent
Majumdar et al.

(10) Patent No.: US 7,049,410 B2
(45) Date of Patent: May 23, 2006

(54) ANTIBODIES TO A NOVEL EGF-RECEPTOR RELATED PROTEIN (ERRP)

(76) Inventors: Adhip P. N. Majumdar, 4516 Kevin Ct., W. Bloomfield, MI (US) 48322; Fazlul H. Sarkar, 13926 Knollview Ct., Plymouth, MI (US) 48170

( * ) Notice: Subject to any disclaimer, the term of this patent is extended or adjusted under 35 U.S.C. 154(b) by 176 days.

(21) Appl. No.: 10/302,868

(22) Filed: Nov. 25, 2002

(65) Prior Publication Data

US 2003/0096373 A1    May 22, 2003

Related U.S. Application Data

(60) Continuation-in-part of application No. 09/867,521, filed on May 31, 2001, now Pat. No. 6,582,934, which is a division of application No. 09/570,454, filed on May 12, 2000, now Pat. No. 6,399,743.

(60) Provisional application No. 60/134,200, filed on May 14, 1999, provisional application No. 60/334,077, filed on Nov. 30, 2001.

(51) Int. Cl.
*C07K 16/00*    (2006.01)

(52) U.S. Cl. .............................. 530/388.22; 530/387.1; 530/388.1; 530/350; 530/413

(58) Field of Classification Search ........... 530/388.22, 530/387.1, 388.1, 350, 413
See application file for complete search history.

(56) References Cited

U.S. PATENT DOCUMENTS

| | | | |
|---|---|---|---|
| 5,218,090 A * | 6/1993 | Connors ..................... 530/350 |
| 5,550,214 A | 8/1996 | Eberlein et al. ............ 530/328 |
| 5,578,482 A | 11/1996 | Lippman et al. ......... 435/240.1 |
| 5,635,399 A | 6/1997 | Kriegler et al. .......... 435/320.1 |
| 5,641,484 A | 6/1997 | Hung et al. ................ 424/93.2 |
| 5,643,567 A | 7/1997 | Hung et al. ................ 424/93.2 |
| 5,650,415 A | 7/1997 | Tang et al. .................. 514/312 |
| 5,651,964 A | 7/1997 | Hung et al. ................ 424/93.2 |
| 5,652,130 A | 7/1997 | Kriegler et al. ............. 435/366 |
| 5,677,171 A | 10/1997 | Hudziak et al. ........ 435/240.27 |
| 5,693,522 A | 12/1997 | Chada et al. ................ 435/402 |
| 5,700,822 A | 12/1997 | Hirth et al. .................. 514/380 |
| 5,710,173 A | 1/1998 | Tang et al. .................. 514/447 |
| 5,720,937 A | 2/1998 | Hudziak et al. ............ 424/9.34 |
| 5,721,277 A | 2/1998 | Tang ........................... 514/646 |
| 5,725,856 A | 3/1998 | Hudziak et al. ......... 424/130.1 |
| 5,760,066 A | 6/1998 | Tang ........................... 514/378 |
| 5,763,470 A | 6/1998 | Tang et al. .................. 514/406 |
| 5,770,195 A | 6/1998 | Hudziak et al. ......... 424/130.1 |
| 5,772,997 A | 6/1998 | Hudziak et al. ......... 424/130.1 |
| 5,773,459 A | 6/1998 | Tang et al. .................. 514/445 |
| 5,773,476 A | 6/1998 | Chen et al. .................. 514/620 |
| 5,789,427 A | 8/1998 | Chen et al. .................. 514/352 |
| 5,792,783 A | 8/1998 | Tang et al. .................. 514/397 |
| 5,804,396 A | 9/1998 | Plowman ................... 435/7.23 |
| 5,807,989 A | 9/1998 | Margolis et al. ............ 530/350 |
| 5,814,315 A | 9/1998 | Hung et al. ................ 424/93.2 |
| 5,814,630 A | 9/1998 | Barker et al. ............. 514/234.5 |
| 5,821,246 A | 10/1998 | Brown et al. ................ 514/253 |
| 5,834,504 A | 11/1998 | Tang et al. .................. 514/418 |
| 5,837,510 A | 11/1998 | Goldsmith et al. ....... 435/172.3 |
| 5,837,523 A | 11/1998 | Greene et al. ............. 435/320.1 |
| 5,849,586 A | 12/1998 | Kriegler et al. ............. 435/372 |
| 5,856,089 A | 1/1999 | Wang et al. ................... 435/6 |
| 5,861,290 A | 1/1999 | Goldsmith et al. ....... 435/172.3 |
| 5,863,797 A | 1/1999 | Kriegler et al. ............. 435/366 |
| 5,869,445 A | 2/1999 | Cheever et al. ................ 514/2 |
| 5,869,618 A | 2/1999 | Lippman et al. ......... 530/387.1 |
| 5,874,077 A | 2/1999 | Kriegler et al. ........... 424/93.21 |
| 5,880,141 A | 3/1999 | Tang et al. .................. 514/339 |
| 5,883,113 A | 3/1999 | Tang et al. .................. 514/418 |
| 5,883,116 A | 3/1999 | Tang et al. .................. 514/418 |
| 5,886,020 A | 3/1999 | Tang et al. .................. 514/418 |
| 5,888,965 A | 3/1999 | Kmiecik et al. ................ 514/2 |
| 5,889,156 A | 3/1999 | Kriegler et al. ............. 530/351 |
| 5,891,917 A | 4/1999 | Tang et al. .................. 514/604 |
| 5,914,343 A | 6/1999 | Tang ........................... 514/398 |
| 5,932,574 A | 8/1999 | Baker ....................... 514/234.5 |
| 5,932,602 A | 8/1999 | Hirth et al. .................. 514/380 |
| 5,935,993 A | 8/1999 | Tang et al. .................. 514/445 |
| 5,942,514 A | 8/1999 | Barker ......................... 514/259 |
| 5,955,464 A | 9/1999 | Barker ......................... 514/259 |
| 5,958,959 A | 9/1999 | Hirth et al. .................. 514/378 |
| 5,962,458 A | 10/1999 | Lohmann et al. ........... 514/259 |
| 5,972,639 A | 10/1999 | Parandoosh .................. 435/29 |
| 5,977,102 A | 11/1999 | Himmelsbach et al. .. 514/234.2 |
| 5,985,553 A | 11/1999 | King et al. ..................... 435/6 |
| 5,990,141 A | 11/1999 | Hirth et al. .................. 514/378 |
| 5,997,859 A | 12/1999 | Barber et al. ............... 424/93.2 |
| 5,998,136 A | 12/1999 | Kamb ............................ 435/6 |
| 6,015,567 A | 1/2000 | Hudziak et al. ........... 424/277.1 |
| 6,015,814 A | 1/2000 | Barker ......................... 514/259 |

(Continued)

FOREIGN PATENT DOCUMENTS

WO    WO 98/14459    9/1998

OTHER PUBLICATIONS

E. Benjamini et al., "Antigenicity". Immunology, A Short Course, 2nd Ed.., 1992 (John Wiley & Sons, Inc.), p. 40.*

(Continued)

*Primary Examiner*—Lorraine Spector
*Assistant Examiner*—Dong Jiang
(74) *Attorney, Agent, or Firm*—Blank Rome LLP

(57) ABSTRACT

This invention relates to ERRP (EGF-Receptor Related Protein) specific antibodies that could be used 1) to study the functional properties of ERRP and; 2) as a diagnostic and prognostic tool for malignancies. Preferably, the antibody reacts with a segment of ERRP containing 15 amino acids (SEQ ID NO: 4) that possesses the most antigenic property.

15 Claims, 10 Drawing Sheets

U.S. PATENT DOCUMENTS

| | | | | |
|---|---|---|---|---|
| 6,040,290 A | 3/2000 | Lippman et al. | ............... | 514/12 |
| 6,051,593 A | 4/2000 | Tang et al. | ................. | 514/397 |
| 6,071,512 A | 6/2000 | Kriegler et al. | .......... | 424/93.21 |
| 6,071,921 A | 6/2000 | Lohmann et al. | ........... | 514/259 |

OTHER PUBLICATIONS

Ullrich et al., Signal Transduction by Receptors with Tyrosine Kinase Activity, Cell, vol. 61, pp. 203-212, 1990.

Reiter et al., A 1.8 kb alternative transcript from the human epidermal growth factor receptor gene encodes a truncated form of the receptor, Nucleic Acids Research, 1996, vol. 24, No. 20, pp. 4050-4056.

Margolis et al., EGF Induces Tyrosine Phosphorylation of Phospholipase C-II: A Potential Mechanism for EGF Receptor Signaling, Cell vol. 57, pp. 1101-1107, 1989.

Kypta et al., Association between the PDGF Receptor and Members of the src Family of Tyrosine Kinases, Cell, vol. 62, pp. 481-492, 1990.

Otsu et al., Characterization of Two 85 kd Proteins that Associate with Receptor Tyrosine Kinases, Middle-T/$pp60^{c-src}$ Complexes, and PI3-Kinase, Cell, vol. 65, pp. 91-104, 1991.

Skolnik et al., Cloning of PI3 Kinase-Associated p85 Utilizing a Novel Method for Expression/Cloning of Target Proteins for Receptor Tyrosine Kinases, Cell, vol. 65, pp. 83-90, 1991.

Escobedo et al., cDNA Cloning of a Novel 85 kd Protein that has $SH_2$ Domains and Regulates Binding of PI3-Kinase to the PDGF β-Receptor, Cell, vol. 65, pp. 75-92, 1991.

Kazlauskas et al., Autophosphorylation of the PDGF Receptor in the Kinase Insert Region Regulates Interactions with Cell Proteins, Cell, vol. 58; 1121-1131, 1989.

Kaplan et al., PDGF β-Receptor Stimulates Tyrosine Phosphorylation of GAP and Association of GAP with a Signaling Complex.

Morrison et al., Direct Activation of the Serine/Threonine Kinase Activity of Raf-1 through Tyrosine Phosphorylation by the PDGF β-Receptor, Cell, vol. 58, pp. 649-657, 1989.

Meisenhelder et al., Phospholipase C-y Is a Substrate for the PDGF and EGF Receptor Protein-Tyrosine Kinases In Vivo and In Vitro, Cell, vol. 57, pp. 1109-1122, 1989.

Ruderman et al., Activation of phosphatidylinositol 3-kinase by insulin, Proc. Natl. Acad. Sci., USA, vol. 87, pp. 1411-1415, 1990, Cell Biology.

Kazlaukas et al., Binding of GAP to Activated PDGF Receptors; Science, 1990, pp. 1578-1581.

Coughlin et al., Role ofd Phosphatidylinositol Kinase in PDGF Receptor Signal Transduction, Science, vol. 243, 1989, pp. 1191-1194.

Morrison et al., Signal transduction from membrane to cytoplasm: Growth factors and membrane-bound oncogene products increase Raf-1 phosphorylation and associated protein kinase activity; Proc. Natl. Acad. Asc. USA, vol. 89, pp. 8855-8859, 1988 Biochemistry.

Molloy et al., PDGF induction of tyrosine phosphorylation of GTPase activating protein, Letters to Nature, vol. 342, pp. 711-714, 1989.

Varticovski et al., The colony stimulating factor-1 receptor associates with and activates phosphatidylinositol-3 kinase, Letters to Nature, vol. 342, pp. 699-702, 1989.

Fazioli et al., The erbB-2 Mitogenic Signaling Pathway: Tyrosine Phosphorylation of Phospholipase C-y and GTPase-Activating Protein Does Not Correlated with erbB-2 Mitogenic Potency, Molecular and Cellular Biology, 1991, pp./ 2040-2048.

Segatto et al., The Juxtamembrane Regions of the Epidermal Growth Factor Receptor and $gp185^{erbB-2}$ Determine the Specificity of Signal Transduction, Molecular and Cellular Biology, 1991, pp. 3191-3202.

Gould et al., Platelet-Derived Growth Facotr Induces Multisite Phosphorylation of $pp60^{c-src}$ and Increases Its Protein-Tyrosine Kinase Activity, Molecular and Cellular Biology, 1988, pp. 3345-3356.

Wahl et al., Platelet-Derived Growth Factor Induces Rapid and sustained Tyrosine Phosphorylation of Phospholipase C-y in Quiescent BALB/c 3T3 Cells, Molecular and Cellular Biology, 1989, pp. 2934-3943.

Avivi et al., Comparison of EFT receptor sequences as a guide to study the ligand binding site, Oncogene (1991), 6, pp. 673-676.

Rusch et al., The Epidermal Growth Factor Receptor and its Ligands as Therapeutic Targets in Human Tumors, Cytokine & Growth Factor Review, vol. 2, No. 2, pp. 133-141—1996—pp. 133-141.

Cohen, Epidermal Growth Factor, Bioscience Reports, vol. 6, No. 12, 1986—pp. 1017-1028.

Modjtahedi et al., Antitumor Activity of Combinations of Antibodies Directerd Against Different Epitopes on the Extracellular Domain of the Human EGF Receptor, Cell Biophysics, vol. 22, 1993—pp. 129-146.

Buolamwini—Novel anticancer drug discover—pp. 500-509.

Dean et al., Immunotherapy with Antibodies to the EGF Receptor, Int. J. Cancer: Supplement 8, 1994—pp. 103-107.

Scher et al., Changing Pattern of Expressiono of the Epidermal Growth Factor Receptor and Transforming Growth Factor ∂ in the Progression of Prostatic Neoplasms, Clinical Cancer Res., vol. 1, 1995—pp. 545-550.

Kita et al., ErbB Receptor Activation, Cell Morphology Changes, and Apoptosis Induced by Anti-Her2 Monoclonal Antibodies, Biochemical and Biophysical Research Comm., vol. 222, 1996, pp. 59-69.

Funding cancer research—EditorialNature Medicine, vol. 4, No. 3, 1998.

Normanno et al., Growth Inhibition of Human Colon Carcinoma Cells by Combinations of Anti-Epidermal Growth Factor-related Growth Factor Antisense Oligonucleotides, Clinical Cancer Research, vol. 2, 1996, pp. 601-609.

Favoni et al., The Role of Polypeptide Growth Factors in Human Carcinomas: New Targvts for a Novel Pharmacological Approach, Pharmacological Reviews, vol. 52, No. 2, pp. 179-206.

Grandis et al., Asynchronous Modulation of Transforming Growth Factor a and Epidermal Growth Factor Receptor Protein Expression in Progression of Premalignant Lesions to Head and Neck Squamous Cell Carcinoma, Clinical Cancer Research, vol. 4, 1998, pp. 13-20.

Nass et al., Epidermal Growth Factor-dependent Cell Cycle Progressio n is Altered in Mammary Epithelial Cells that overexpress c-myc, Clinical Cancer Research, vol. 4, 1998, pp. 1813-1822.

Friess et al., Molecular Aspects of Pancreatic Cancer and Future Perspectives, Dig. Surg. vol. 16, 1999, pp. 281-290.

Tecce et al., Characterization of Cytotoxic Activity of Saporin Anti-GP185/HER-2 Immunotoxins, Int. J. Cancer, vol. 55, 1993, pp. 122-127.

Nicholson et al., Epidermal growth factor receptor (EGFr); results of a 76 year follow-up study in operable breast cancer with emphasis on the node negative subgroup, Br. J. Cancer, vol. 63, 1991, pp. 146-150.

Kirk et al., Selective toxicity of TGF-1-Pe40 to EGFR-positive cell lines: selective protection of low EGFR-expressing cell lines by EGF, Br. J. Cancer, vol. 69, 1994, pp. 988-994.

Harris et al., Epidermal Growth Factor Receptor and Other Oncogenes as Prognostic Markers, J. Nat. Cancer Institue Monographs, No. 11, pp. 181-187.

Witters et al., Antisense oligonucleotides to the epidermal growth factor receptor, Breast Cancer Research and Treatement, vol. 53, 1999, pp. 41-50.

Derynck et al., Synthesis of Messenger RNAs for Transforming Growth Factors a and B and the Epidermal Growth Factor Receptor by Human Tumors, Cancer Research, vol. 47, 1987, pp. 707-712.

Scher et al., Use of Adaptive Control with Feedbacfk to Individualize Suramin Dosing, Cancer Research, vol. 52, 1992, pp. 64-70.

Fontanini et al., Epidermal Growth Factor Receptor (EGFr) Expression in Non-small Cell Lung Carcinomas Correlates with Metastatic Involvement of Hilar and Mediastinal Lymph Nodes in the Squamous Subtype, Eur J. Cancer, vol. 31A, No. 2, 1995, pp. 178-183.

Eisenberger et al., Suramin, New Drugs, Cancer Treatment Reviews, vol. 20, 1994, pp. 259-273.

Baselga et al., Antitumor Effects of Doxorubicin in Combination With Anti-epidermal Growth Factor Receptor Monoclonal Antibodies, Journal of the National Cancer Institute, vol. 85, No. 16, 1993, pp. 1327-1333.

Divgi et al., Phase I and Imaging Trial and Indium 111-Labeled Anti-Epidermal Growth Factor Receptor Monclonal Antibody 225 in Patients with Squamous Cell Lung Carcinoma, Journal of the National Cancer Institute, vol. 83, No. 2, 1991, pp. 97-104.

Fry et al., A Specific Inhibitor of the Epidermal Growth Factor Receptor Tyrosine Kinase, Science, vol. 265, 1994, pp. 1093-1095.

Perez-Soler et al., Tumor Epidermal Growth Factor Receptor Studies in Patients with Non-Small-Cell Lung Cancer or Head and Neck Cancer Treated with Monoclonal Antibody RG 83852, Journal of Clinical Oncology, vol. 12, No. 4, 1994, pp. 730-739.

Pegram et al., Phase II Study of Receptor-Enhanced Chemosensitivity Using Recombinant Humanized Anti-p185HER2/neu Monoclonal Antibody Plus Cisplatin in Patients with HER2/neu-Overexpressing Metastatic Breast Cancer Refractory to Chemotherapy Treatment, Journal of Clinical Oncology, vol. 16, No. 8, 1998, pp. 2659-2671.

Fan et al., Antitumor Effect of Anti-Epidermal Growth Factor Receptor Monoclonal Antibodies plus cis-Diamminedichloroplatinum on Well Established A431 Cell Xenografts, Cancer Research, vol. 53, 1993, pp. 4637-4642.

* cited by examiner

ERRP antibody reacts strongly with benign colonic epithelium but weakly with colonic adenocarcinoma.

ERRP antibody reacts with benign prostatic glands but not with invasive prostatic adenocarcinoma

ANTIBODIES TO A NOVEL EGF-RECEPTOR RELATED PROTEIN (ERRP)

This application is a Continuation-in-Part (CTP) of U.S. patent application Ser. No. 09/867,521, filed May 31, 2001 now U.S. Pat. No. 6,582,934, which is a divisional of U.S. patent application Ser. No. 09/570,454, filed May 12, 2000, now U.S. Pat. No. 6,399,743. This application also claims priority to Provisional Applications Serial Nos. 60/134,200, filed May 14, 1999 and 60/334,077, filed Nov. 30, 2001.

This work has been supported by the Department of Veterans Affairs. The United States Government retains certain rights in this invention.

BACKGROUND OF THE INVENTION

This invention relates to ERRP (EGF-Receptor Related Protein) specific antibodies that could be used 1) to study the functional properties of ERRP and; 2) as a diagnostic and prognostic tool for malignancies.

Growth factors and hormones exert pleiotropic effects on cellular functions, including mitogenic stimulation and modulation of differentiation and metabolism (Ullrich et al., Cell 61:203–212 (1990); Aaronson, Science 254: 1146–1153 (1991)). In many cases, these actions are mediated by the interaction of growth factors with cell surface tyrosine kinase receptors (TKRs), which results in enhanced receptor catalytic activity and tyrosine phosphorylation of intracellular substrates (Ullrich et al., supra, Aaronson, supra). Knowledge of the nature of these second messenger systems is still scanty, although some molecules which associate and/or are tyrosine phosphorylated by TKRs have been identified. These include the γ isozyme of phospholipase C (PLC-7) (Margolis et al., Cell 57: 1101–1107 (1989); Meinsenhelder et al., Cell 57: 1109–1122 (1989); and Wahl et al., Mol. Cell. Biol. 9: 2934–2943 (1989)); the p21ras GTPase activating protein (GAP) (Molloy et al., Nature 342: 711–714 (1989); Kaplan et al., Cell 61:125–133 (1990); and Kazlauskas et al., Science 247: 1578–1581 (1990)); the raf serine-threonine kinase (Morrison et al., Proc. Natl. Acad. Sci. USA 85: 8855–8859 (1988); and Morrison et al. Cell 58: 649–657 (1989)); the p85 subunit of the phosphatidylinositol 3-kinase (PtdIns-3K) (Coughlin et al., Science 243: 1191–1194 (1989); Kazlauskas et al., Cell 58: 1121–1133 (1989); Varticovski et al., Nature 342: 699–702 (1989); Ruderman et al., Proc. Natl. Acad. Sci. USA 87: 1411–1415 (1990); Escobedo et al., Cell 65: 75–82 (1991); Skolnik et al., Cell 65: 83–90 (1991); and Otsu et al., Cell 65: 91–104 (1991)) and some cytoplasmic tyrosine kinases (Gould et al., Mol. Cell. Biol. 8: 3345–3356 (1988); and Kypta et al., Cell 62: 481–492 (1990)). These signaling molecules are thought to mediate at least in part the mitogenic effects of TKRs (Ullrich, et al. supra; Aaronson, supra).

However, the Epidermal growth factor (EGF) receptor (EGFR) does not appear to efficiently interact with known second messenger systems (Fazioli et al., Mol. Cell. Biol. 11: 2040–2048 (1991); and Segatto et al., Mol. Cell. Biol. 11: 3191–3202 (1991)). Thus, there is need to ascertain the mechanism by which the EGFR functions in mitogenesis, and a particular need to identify and characterize the substrate (if any) of the EGFR.

Errors which occur in the mitogenic signaling pathway, such as alterations in one or more elements of that pathway, are implicated in malignant transformation and cancer. It is believed that in at least some malignancies, interference with such abnormal mitogenic signal transduction could cause the cells to revert to normal phenotype.

In addition, reagents useful in identifying molecular components of the mitogenic signaling pathway find utility as tumor markers for therapeutic, diagnostic, and prognostic purposes. Furthermore, identification of how such components differ from normal components in malignant tissue would be of significant value in understanding and treating such malignancies.

EGFR, a 170 kDa transmembrane glycoprotein protein with intrinsic tyrosine kinase activity, which binds EGF family of peptides, plays an important role in controlling cell proliferation and differentiation as was shown by Ullrich et al. supra. The EGFR possesses three functional domains that include extracellular, transmembrane and cytoplasmic. Ligand binding to the extracellular domain of EGFR leads to dimerization and activation of the receptor's intrinsic tyrosine kinase, located in the cytoplasmic domain, triggering a complex array of enzymatic and biological events leading to cell proliferation and differentiation.

Members of the receptor tyrosine kinase family are frequently implicated in experimental models of epithelial cell neoplasia as well as in human cancers (Hunter et al., Ann. Rev. Biochem. 54: 897–930 (1985); Yarden et al., Ann. Rev. Biochem. 57: 443–487 (1987); Candena et al., FESEB J. 6: 2332–2337 (1992); Glenney, Biochim. Biophys. Acta 1134: 113–127 (1992); and Joensuu et al., N. Eng. J. Med. 344: 1052–1056 (2000)). There is increasing evidence to support the concept that the malignant behavior of some tumors is sustained by deregulated activation of certain growth factor receptors. Such deregulation could be either structural alterations of the receptor itself (Downward et al., Nature 307: 521–527 (1984); and Sefton, In: R A Bradshaw and S Prentis (eds.), Oncogenes and Growth Factors. Elsevier Biomedixal Press, Amsterdam (1987)) or to the establishment of an autocrine loop, whereby the cells produce growth factors that stimulate their own growth (Cutlitta et al., Nature 216: 825–826 (1985); Betsholtz et al., Cell 39: 447–457 (1984); and Sporn et al., Nature 313: 745–747 (1985)). The receptors with intrinsic tyrosine kinases are activated following binding of their growth factors. One of the best studied receptor signaling systems from this family is that controlled by the EGF-receptor (EGFR), whose expression and enzyme activity have been linked to a number of malignancies, including cancer of the colon (Culig et al., The Prostate 28: 392–405 (1996); Barnard et al., Gastroenterology 108: 564–580 (1995); Khasharyarsha et al., Cancer and Metastasis Rev. 12: 255–274 (1993); and Gullick, Br. Med. Bull. 47: 87–98 (1991)). EGFR and its ligand TGF-α, a structural and functional analogue of EGF, are overexpressed in preneoplastic and epithelial cells (Malecka-Panas et al., Hepato-Gastroenterology, 44: 435–440 (1997); Relan et al., Biochim. Biophys. Acta 1244: 368–376 (1995); Barnard et al., Gastroenterology 108: 564–580 (1995); and Khasharyarsha et al., Cancer and Metastasis Rev. 12: 255–274 (1993). Moreover, cell lines derived from adenocarcinomas of various gastrointestinal (GI) tissues, including the colon have been found to overexpress TGF-α and its receptor EGFR (Coffey et al., Cancer Res. 46: 1164–1169 (1986); Ohmura et al., Cancer Res. 50: 103–107 (1990); Yoshida et al., Int. J. Cancer 45: 131–135 (1990); Coffey et al., Cancer Res. 46: 1164–1169 (1986); Anzane et al., Cancer Res. 49: 2898–2904 (1989). Because of EGFR's role in the development of progression of many epithelial cancers, efforts are being made to utilize EGFR as a potential target for epithelial cancer therapy. Several approaches, including monoclonal antibodies to EGFR and pharmacological inhibitor(s) of EGFR tyrosine kinase have been utilized. However, the effectiveness of most of the therapeutic regimen has, thus far, been limited primarily because of toxicity and/or lack of specificity.

SUMMARY OF THE INVENTION

The present invention is directed toward a polynucleotide sequence, proteins transcribed from the nucleotide sequence, methods for the use of epidermal growth factor receptor related protein (ERRP) as well as probes for the detection of m-RNA, DNA and cDNA of the described nucleotide sequence and antibodies directed toward ERRP. The antibodies are useful as a diagnostic and prognostic tool for tumor malignancies.

In particular, a cDNA fragment clone of 1583 base pairs with 90–95% sequence homology to mouse epidermal growth factor receptor (EGFR) and a truncated rat EGFR was isolated. The full length cDNA revealed 1958 base pairs (SEQ ID No: 1) that contained 227 base pairs of 5' untranslated region and an open reading frame encoding 478 amino acids (SEQ. ID NO: 2) followed by 290 base pairs of an untranslated region. The full length cDNA showed an 84% and 91% homology, respectively, to a rat truncated EGFR and the mouse EGFR. The product of the newly isolated DNA is referred to as ERRP (EGF-Receptor Related Protein). In a Northern-blot analysis with poly A+RNA from different rate tissues, ERRP cDNA hybridized strongly to a mRNA transcript of about 1.8 Kb. Maximal expression was noted in the small intestine, followed by colon, liver gastric mucosa and other tissue. Transfection of ERRP cDNA in HCT-116 cells, a colon cancer cell line, markedly inhibited (40–60%) proliferation in monolayer and soft agar and also attenuated EGFR tyrosine kinase activity compared to vector-transfected control cells. Proliferation of the vector-transfected control, but not ERRP transfected HCT cells could be stimulated by TGF-α. The over expression of ERRP in HCT-116 cell delayed tumor growth in SCID mice xenografts. The ERRP cDNA represents a new member of the EGFR gene family and the protein product plays a key role in modulating the function of EGFR.

DETAILED DESCRIPTION OF THE INVENTION

Figure 1:
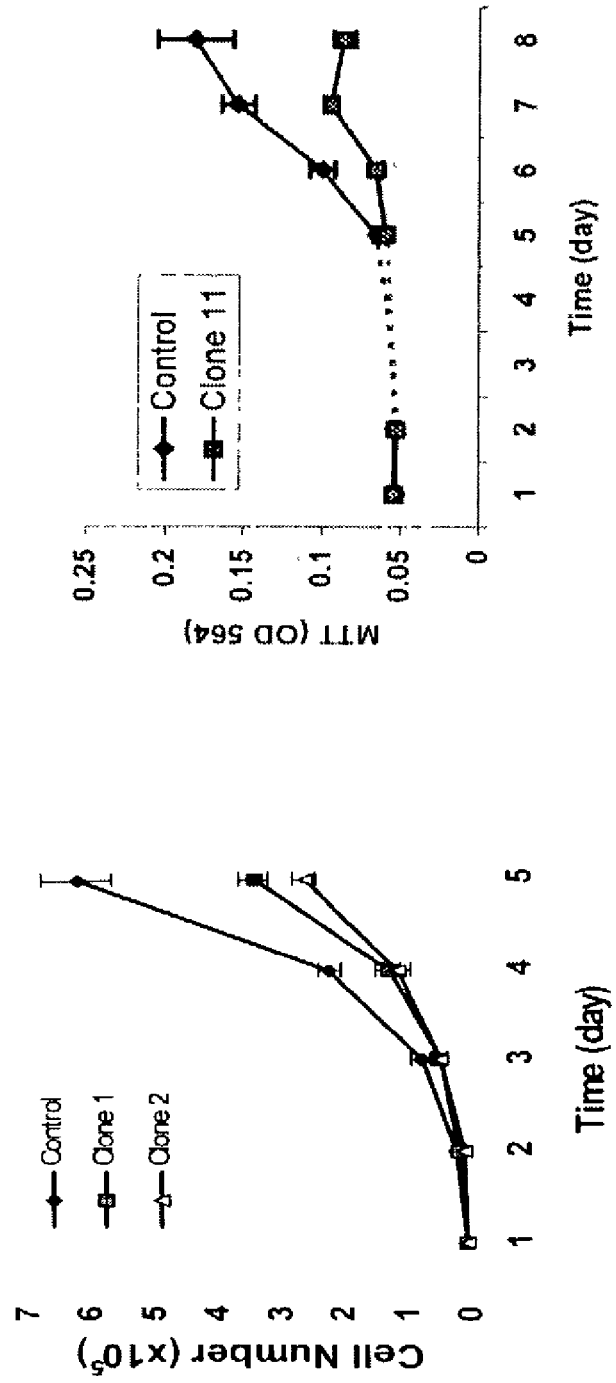
FIG. 1 shows changes in proliferation of HCT-116 (colon) and PC-3 (prostate) cancer cells following transfection with ERRP cDNA or the vector (control).

Detailed description of isolation and chracterization of ERRP is disclosed in U.S. Pat. No. 6,399,743, the disclosure of which is incorporated herein by reference. Briefly, the full-length cDNA (SEQ ID NO: 1) consisted of 1958 bp that included an open reading frame (ORF) of 1437 nucleotides encoding for 478 amino acids (SEQ ID NO: 2). The full-length cDNA (SEQ ID NO: 1) was found to be about 85% homologous to the external domain of rat EGFR. It also possesses about 80% homology to the external domain of human EGFR. Because of its significant homology with EGFR, we refer to the product of this cDNA as ERRP (EGF Receptor Related Protein). A region of the 3' end, referred to herein as the "U" region (nucleotides 1580–1661 of SEQ ID NO: 1) encoding 27 amino acids (SEQ ID NO: 3) shows no homology with any known sequence in the current data base. Further, computer analysis of the "U" region revealed a segment containing 15 amino acids (SEQ ID NO: 4) that possesses the most antigenic property. The protein (SEQ ID NO: 2) and these regions (SEQ ID NOS: 3–4) are utilized to generate antibodies to ERRP as described below.

I. Production of Monoclonal Antibody

The monoclonal antibody specific to ERRP can be produced as follows.

(A) Preparation of Antigen

The protein or fragment thereof, most preferably the "U" region (SEQ ID NO: 3) or the segment containing 15 amino acids (SEQ ID NO. 4), are prepared as described above is dissolved in a buffer solution, and an adjuvant is then added thereto. As such an adjuvant, commercially available Freund's complete or incomplete adjuvant or the like may be used singly or in the mixed form.

(B) Immunization and Isolation of Antibody-producing Cells

The immunogen prepared as described above is administered to a mammalian animal (e.g., rat, mouse). A single dose of the antigen used for the immunization may be 10–500 μg per animal. The animal may be immunized by injecting the antigen intravenously, subcutaneously, or intraperioneally. The interval of the immunization is not particularly limited, and the immunization may be performed at intervals of several days to several weeks, preferably 1–3 weeks, for 2–5 times, preferably 3–4 times. Two to seven days, preferably four to five days, after the final immunization, antibody-producing cells are isolated. Such antibody-producing cells may be spleen cells, lymph node cells, peripheral blood cells, and preferably spleen cells or localized lymph node cells.

(C) Cell Fusion

The myeloma cells used for cell fusion with the antibody-producing cells may be of a usually commonly available established cell line of an animal (e.g., mouse). The cell line used is preferably one having drug selectivity, and incapable of surviving in a selective medium (HAT medium; comprising hypoxanthine, aminopterin and thymidine) in its non-fused form but capable of surviving in such a selective medium only in its fused form with an antibody-producing cell. Specific examples of the myeloma cell include mouse myeloma cell line such as P3U-1 (Dainippon Pharmaceutical Co., Ltd.) and P3x63Ag8.653. The myeloma cells are then fused with the antibody-producing cells. The cell fusion may be performed by mixing the antibody-producing cells with the myeloma cells at a ratio of 100–500 cells of the antibody-producing cells per 1 myeloma cell, for example, by mixing equivalent volumes of a culture medium containing $10^8$ cells/ml of the antibody-producing cells and a culture medium containing $2 \times 10^5$ cells/ml of the myeloma cells, and the mixture is then subjected to fusion reaction in the presence of a fusion promoting agent. For promoting the cell fusion, polyethylene glycol with a mean molecular weight of 1,500 daltons or the like may be used. Alternatively, a commercially available cell fusion apparatus utilizing electrical stimulation (e.g., electroporation) may be employed to cause the cell fusion of the antibody-producing cells with the myeloma cells.

(D) Screening and Cloning of Hybridomas

The desired hybridomas are screened from the cells after the cell fusion treatment. The screening may be performed by appropriately diluting the cell suspension with RPMI-1640 medium containing fetal bovine serum or the like, inoculating the resultant dilution solution into each well of a microtiter plate in an amount of about 5–10 cells/well, adding a selective medium to each well, and then incubating the plate while appropriately replacing the selective medium in the wells by a fresh one. The desired hybridomas can be obtained as the cells grown about 14 days after the culture is started. The culture supernatant of the grown hybridomas is then screened for the presence of the antibodies of interest. The screening may be performed by a conventional method, and the method is not particularly limited. For example, a portion of the hybridoma-containing culture supernatant may be removed from the individual wells and subjected to screening by enzyme immunoassay (EIA), radio immunoassay (RIA) or the like.

The cloning of the fused cells is then performed by a limiting dilution method or the like to ultimately establish hybridomas which produce monoclonal antibodies.

(E) Collection of Monoclonal Antibodies

As the method for collecting monoclonal antibodies from the above-established hybridomas, a conventional cell culture method or ascites fluid production method may be employed. In the case of a cell culture method, the hybridomas are cultured in a culture medium for animal cells, such as RPMI-1640 medium containing 10% fetal bovine serum, MEM medium or a serum-free medium, under conventional culture conditions (e.g., 37° C., 5% CO.sub.2) for 10–14 days, and the antibodies can be obtained from the culture supernatant. In the case of an ascites fluid production method, the hybridomas (about $5 \times 10^6$ cells) are administered intraperitoneally to an animal of the same species as that of the mammal from which the myeloma cells are derived, thereby causing to grow the hybridomas in a large scale. One to two weeks later, the ascites fluid or serum is collected from the animal. In these antibody-collecting methods, if it is required to purify the antibodies, a known method such as salting out with ammonium sulfate, ion exchange chromatography, affinity chromatography or gel chromatography may be employed singly or in combination.

II. Production of Polyclonal Antibodies (A) Preparation of Antigen

The protein or fragment thereof, most preferably the "U" region (SEQ ID NO: 3) or the segment containing 15 amino acids (SEQ. ID NO. 4), as described above is dissolved in a buffer solution, and then an adjuvant is added thereto. Such an adjuvant may be commercially available Freund's complete or incomplete adjuvant.

(B) Immunization

The animal used for the immunization can be, but is not limited to, a rabbit, guinea pig, goat, sheep or the like. In the case of a rabbit, for example, the protein is injected subcutaneously to the foot paw usually at a dose of 100–500 μg together with Freund's complete adjuvant. Two weeks later, the same dose of the antigen mixed with Freund's incomplete adjuvant is injected intramuscularly. Additional two weeks later, the intramuscular injection is repeated. One week after the final immunization, a portion of the blood was collected from the ear and determined for the antibody titer by EIA method or the like. When the antibody titer reaches the desired value, the whole blood was collected. However, if the antibody titer is low, the immunization is repeated until the antibody titer reaches the desired value. The antibodies are then purified from the serum by ammonium sulfate fractionation as mentioned in the above-described relevant section for the purification of the monoclonal antibodies.

The following examples are given to illustrate the present invention. It should be understood that the invention is not limited to the specific conditions or details described in these examples.

EXAMPLE 1

To assess putative functional properties of ERRP, the ERRP cDNA or the vector [PC DNA 3.1(+)] was stably transfected into HCT-116 and PC-3 cells. The reason for transfecting the colon and prostate cancer cell lines was to determine whether the ERRP-induced inhibition could be observed in two different epithelial cancer cell lines from different tissues. Of the fifteen ERRP-positive clones obtained from these cell lines, two clones from HCT-116 cells (clones 1 and 2), and three from PC-3 cells (clones 2, 8 and 11) showing maximal expression of ERRP mRNA as evidenced by Northern-blot and RT-PCR were utilized for further experiments.

EXAMPLE 2

When the ERRP cDNA and the corresponding vector-transfected (controls) clones were maintained in DMEM containing 10% FBS, we observed that ERRP-overexpressed clones of HCT-116 and PC-3 cells grew at a much slower rate, compared to the corresponding vector-transfected controls (FIG. 1 ). After 5–6 days, proliferation of ERRP-overexpressed clones of HCT-116 and PC-3 cells was decreased by 50–70%, compared to the corresponding controls (FIG. 1). Results suggest that overexpression of ERRP inhibits proliferation of both types of cancer cells.

EXAMPLE 3

To test whether ERRP inhibit proliferation by attenuating EGFR activation., we generated sublines from Caco-2 (a colon cancer cell line) cells that contained a tetracycline-inducible promoter system, capable of increasing ERRP expression. In the absence of doxycycline, a condition that augmented ERRP expression (as evidenced by the induction of luciferase activity), there was a marked reduction in the extent of phosphorylation (p-EGFR), tyrosine kinase activity of EGFR (phosphorylation of acid-denatured enolase) and cell proliferation. However, no significant change in EGFR levels was observed between doxycycline-treated and untreated cells. Taken together, the results suggest a role for ERRP in regulating cell proliferation by modulating the function of EGFR.

EXAMPLE 4

Figure 2:
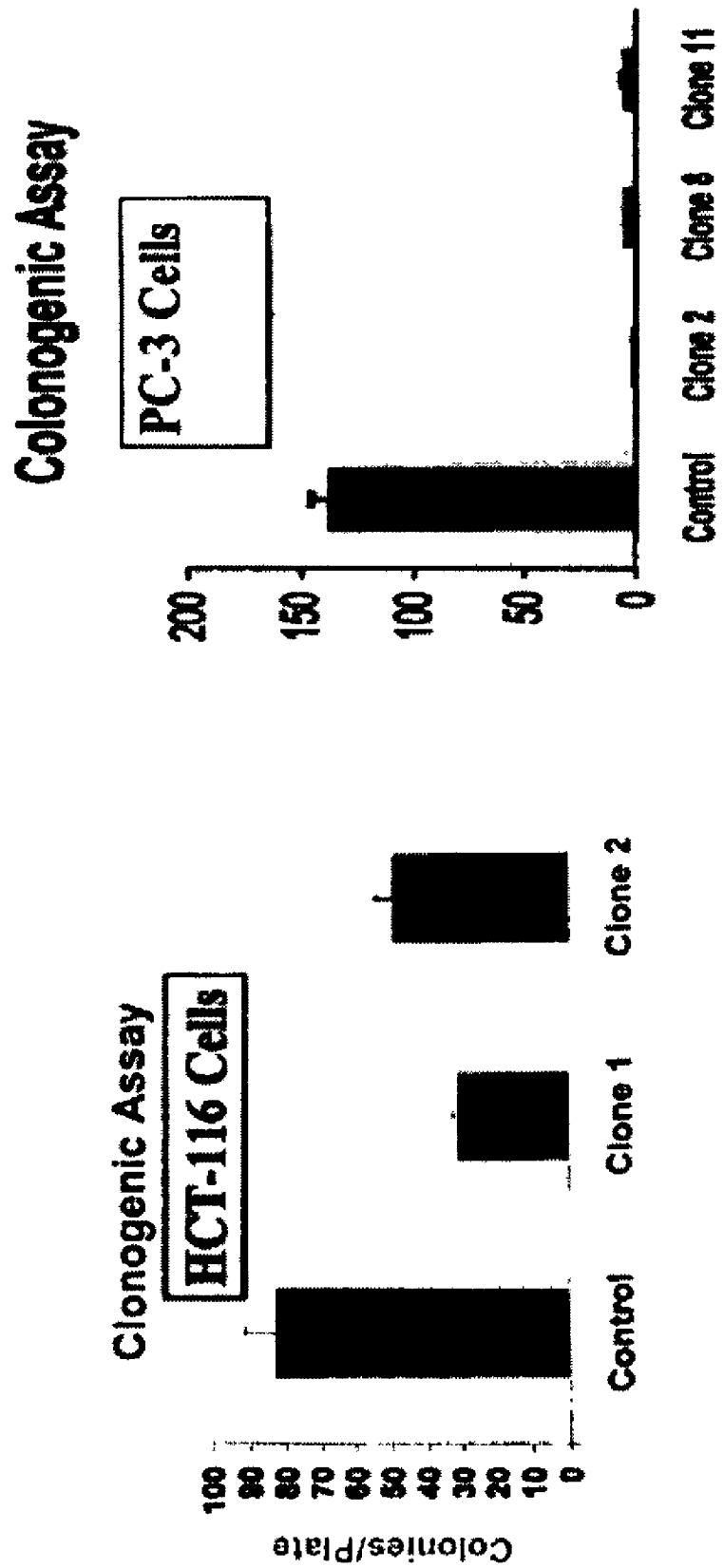
FIG. 2 depicts results of clonogenic assays in soft agar showing the number of colonies formed by HCT-116 (colon) and PC-3 (prostate) cancer cells following transfection with either ERRP cDNA or the vector (control).

To determine whether expression of ERRP affects the transformed properties of HCT-116 and PC-3 cells, clones expressing ERRP in HCT-116 (clones 1 and 2) and PC-3 cells (clones 2, 8 and 11) and their control counterparts were grown in soft agar for 14 days. As shown in FIG. 2, the number of colonies formed by ERRP-expressing clones from PC-3 and HCT-116 cells was greatly reduced, compared to the corresponding control clones.

EXAMPLE 5

Figure 3:
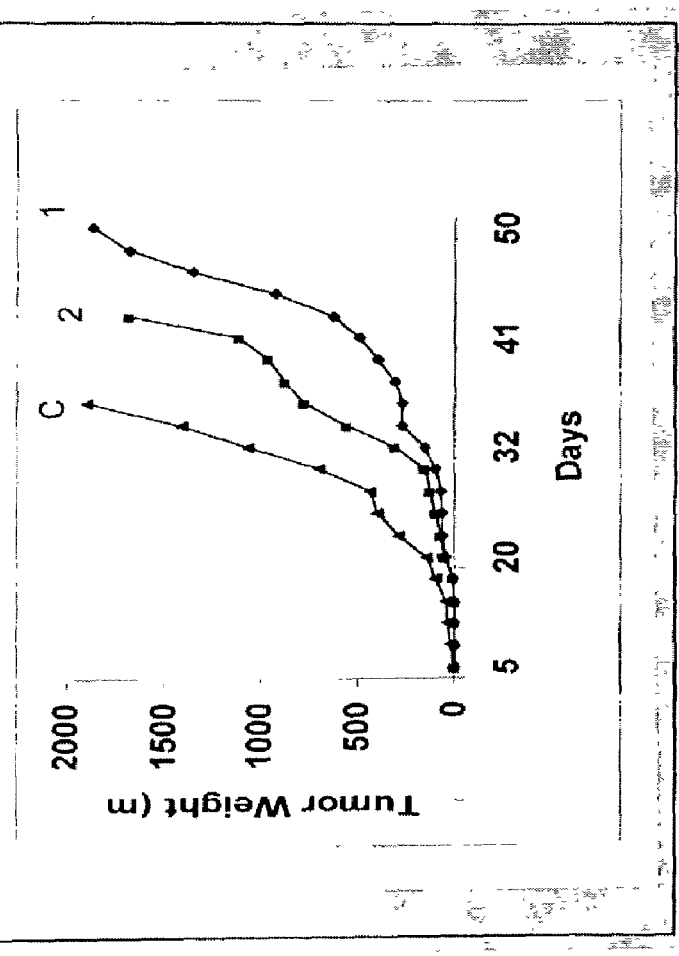
FIG. 3 shows changes in the rate of growth of tumors by HCT-116 cells, transfected with ERRP cDNA (Clones 1 and 2) or the vector only (control).

To determine the tumorigenic properties of ERRP, the growth rate of HCT-116 cells-induced tumors was examined in SCID mice. Groups of SCID mice were injected with either $5\times10^6$ HCT-116 cells (clone 1 or 2 expressing ERRP)/flank or controls (transfected with the vector). Tumor growth was monitored. When the tumor(s) attained the size of approx. 1800 mg, the mice were killed. We observed that in mice injected with control cells, the tumor(s) attained the required weight on the $24^{th}$ day after injection, whereas with clone 1 or 2, it took 14–20 days longer for tumor(s) to grow to that size (FIG. 3). Tumor growth was slowest for clone 1 transfected cells as was colony formation in soft agar. A relatively small delay in tumor growth by ERRP-overexpressed HCT-116 cells compared to the controls could partly be due to administration of a large number of cells ($5\times10^6$ cells/flank of a mouse). Taken together, the results suggest that at least in HCT-116 cells, overexpression of ERRP affects the tumorigenic phenotype.

EXAMPLE 6

Figure 4:
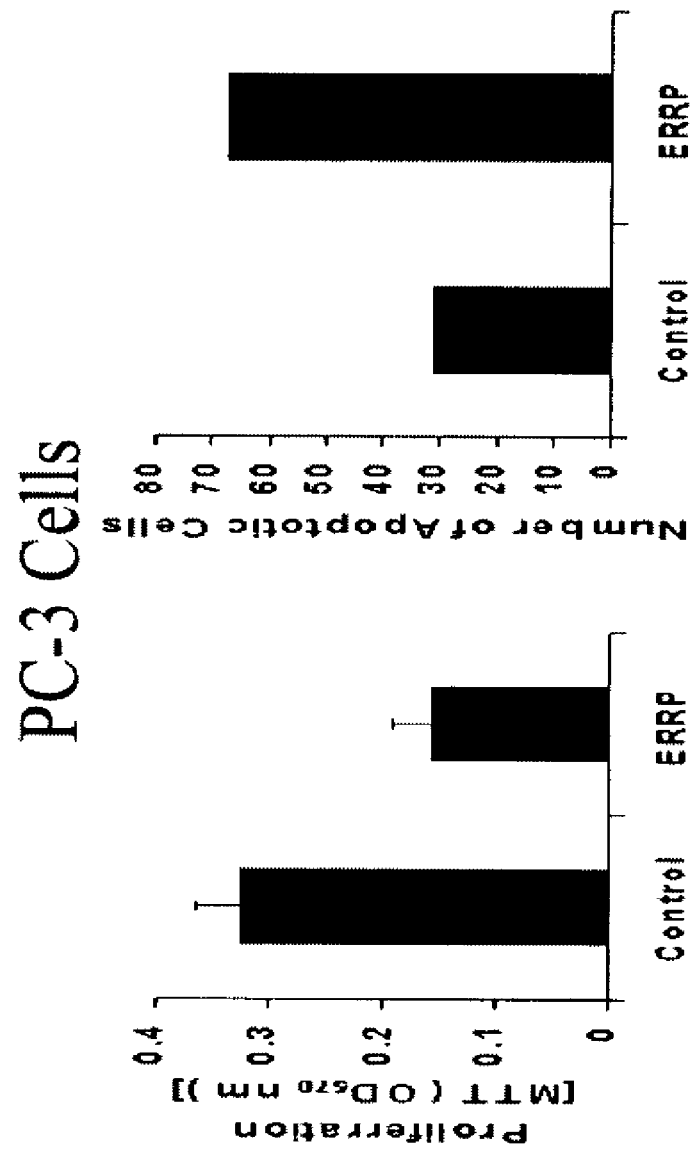
FIG. 4 shows changes in proliferation and apoptosis in PC-3 cells at 72 h after transient transfection with either ERRP cDNA or the vector (control).

We have repeatedly observed that when ERRP tagged with EGFP (enhanced green fluorescence peptide) is transfected into PC-3 or HCT-116 cells, the cells that survived show reduced to minimal intensities of green fluorescence, when compared with the vector transfectants. We suspected that cells overexpressing ERRP-EGFP chimera did not survive the selection procedure. To determine whether high expression of ERRP promotes cell death, equal numbers of PC-3 cells were transiently transfected with plasmid expressing full-length ERRP cDNA (pcDNA3-ERRP) or the vector plasmid (pcDNA3). Seventy two hours later, the cells were examined for proliferation by MTT or apoptosis by staining with acridine orange/ethidium bromide. We observed that whereas transfection of ERRP inhibited proliferation by 55%, it produced a 130% stimulation in apoptosis, when compared with the corresponding vector-transfected controls (FIG. 4).

Figure 5:
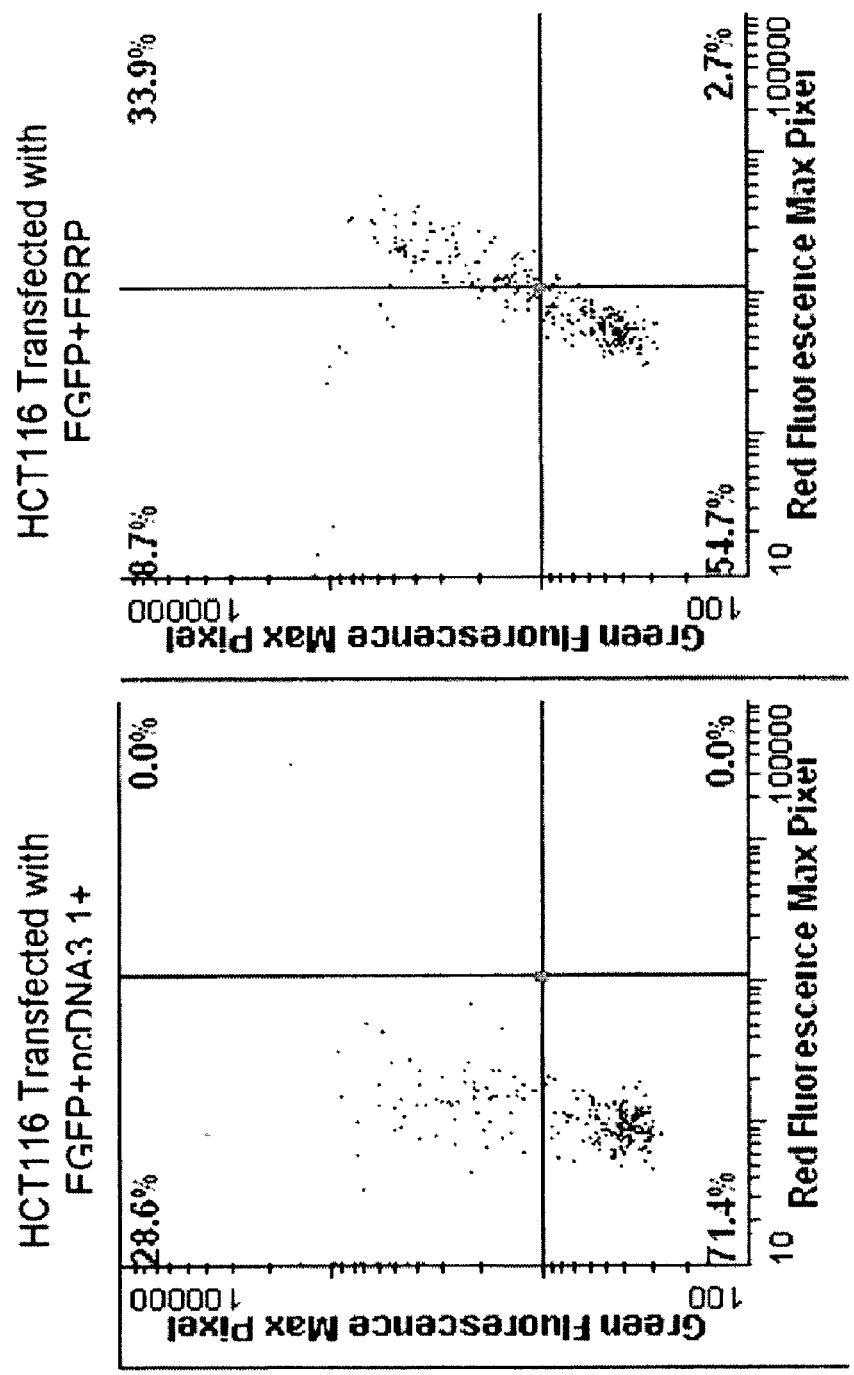
FIG. 5 depicts the results of laser scanning cytometry (LSC) showing ERRP-induced changes in apoptosis in HCT-116 cells.
Figure 6:
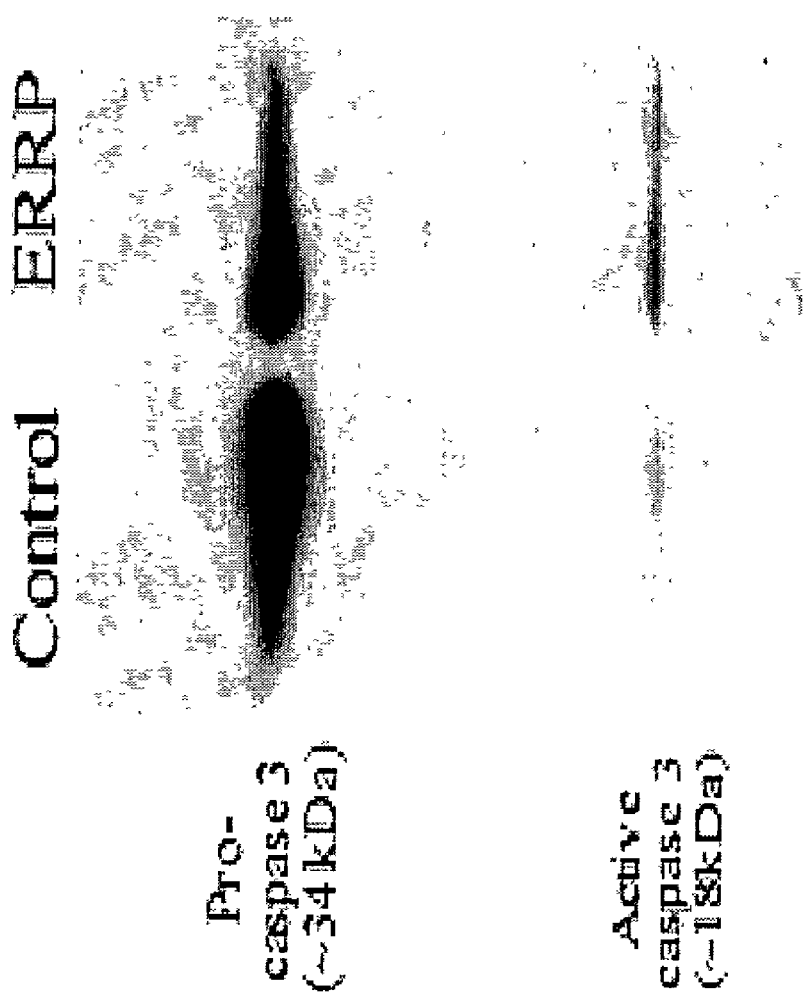
FIG. 6 are Western-blots showing changes in the levels of pro- and active forms of caspase 3 in HCT-116 cells, 16 hours after transient transfection with the full-length ERRP cDNA or the vector (control).

To further examine ERRP induction of apoptosis, HCT-116 cells were transiently co-transfected with enhance green fluorescence (EGFP) plasmid and the pcDNA3.1(+) vector or the full-length ERRP cDNA and EGFP plasmid. Twenty four hours after transfection, the cells were stained with annexin V conjugated with phycoerythrin, detected by red fluorescence. The cells were put on slides and analyzed on a laser scanning cytometer (CompuCyte). The transfection frequency for EGFP+pcDNA3.1(+) was about 29% and for EGFP+ERRP cDNA was 43% (FIG. 5). Of the EGFP+pcDNA3.1(+) transfected cells, none were apoptotic (both red and green positive), whereas 80% of the EGFP+ERRP cDNA transfected cells were apoptotic (FIG. 5). These changes are associated with activation of caspase 3 as evidenced by the decreased levels of the 34 kDa pro-caspase 3 and increase in the 18 kDa active form of the enzyme in HCT-116 cells (FIG. 6), further indicating induction of apoptotic processes. Taken together, the results show that overexpression of ERRP in HCT-116 and PC-3 cells inhibits proliferation and stimulates apoptosis.

EXAMPLE 7

We have raised antibodies to ERRP using the 27-amino acid unique region "U" (24). The "U" region encoding 27 amino acids (SEQ ID NO: 3) shows no homology with any known sequence in the current data bases. Computer analysis of the "U" region revealed that a segment (underlined region) of the peptide containing 15 amino acids (SEQ ID NO: 4) possesses the most antigenic property. Following synthesis of the 15-mer fragment of this region of ERRP, the synthetic peptide was used to raise polyclonal antibodies in rabbits. Synthesis of the 15-amino acid peptide of ERRP and subsequent generation of antibodies against this peptide were carried out by Sigma-Genosys, Woodlands, Tex., a company that specializes in antibody production. ERRP antibodies were used to examine ERRP expression in normal and tumor tissues.

EXAMPLE 8

Figure 7:
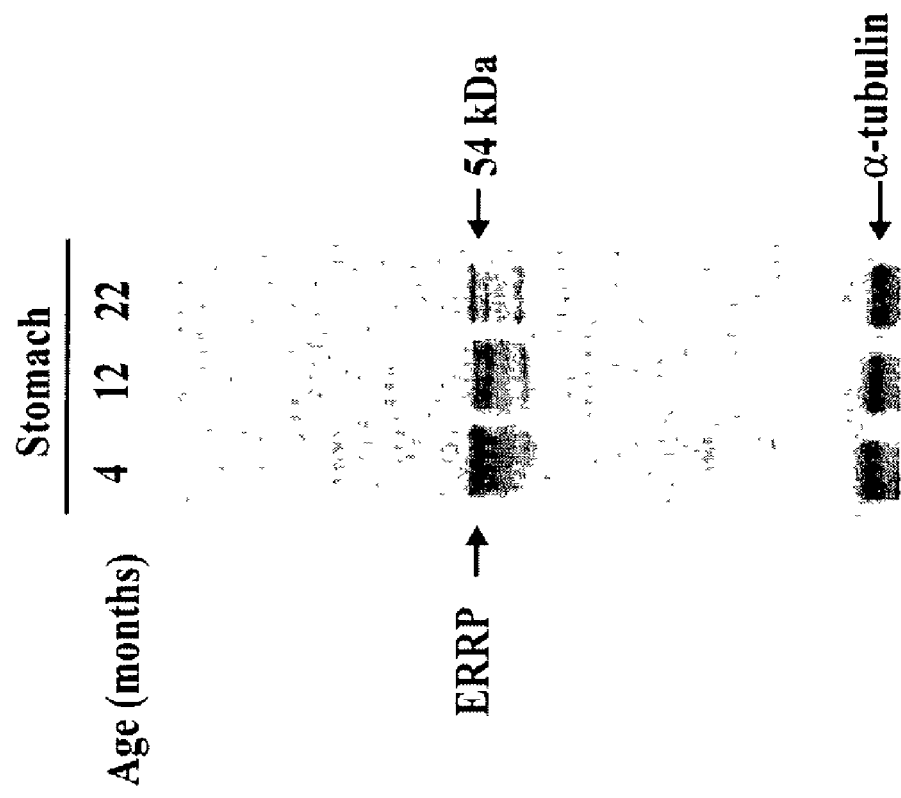
FIG. 7 are Western-blot showing ERRP levels in the gastric mucosa of 4-, 12- and 22-months old rats.

To examine whether that ERRP is a "negative regulator" of EGFR that inhibits proliferation and stimulates apoptosis by attenuating EGFR activation, we analyzed its levels in the gastric mucosa of 4–12- and 22-months old rats by Western-blot using the anti-ERRP-Ab (1:1000 final dilution). Reasons for analyzing gastric mucosa during aging are that (a) ERRP cDNA was isolated from gastroduodenal mucosa and (b) aging is associated with increased EGFR activation and proliferative activity in the gastric mucosa (25,26). If ERRP is an endogenous protein, we expect to detect a protein of a molecular mass of ~55 kDa (478 amino acid×115 average molecular weight of amino acids). Since aging is associated with increased activation of EGFR (25,26), we also expect the levels of ERRP to decrease in the gastric mucosa with aging if ERRP plays a role in regulating EGFR function. As shown in the Western blot (FIG. 7), the anti-ERRP-Ab detected multiple proteins with molecular mass of 50–54 kDa in the gastric mucosa. Whether these protein bands represent glycosylated, non-glycosylated or other posttranslational forms of ERRP remain to be determined. Results of the Western-blot analysis also show that the expression of ERRP declines with aging as demonstrated by reduced levels of the protein bands (FIG. 7). The age-related decline in ERRP levels in the gastric mucosa could not be attributed to differences in loading since no significant changes in α-tubulin levels were observed among the samples (FIG. 7). Furthermore, the fact that the polyclonal antibodies to ERRP show no cross-reactivity with any member of the EGFR-family of proteins (170–190 kDa) suggests that the antibodies are specific to ERRP.

EXAMPLE 9

Figure 8:
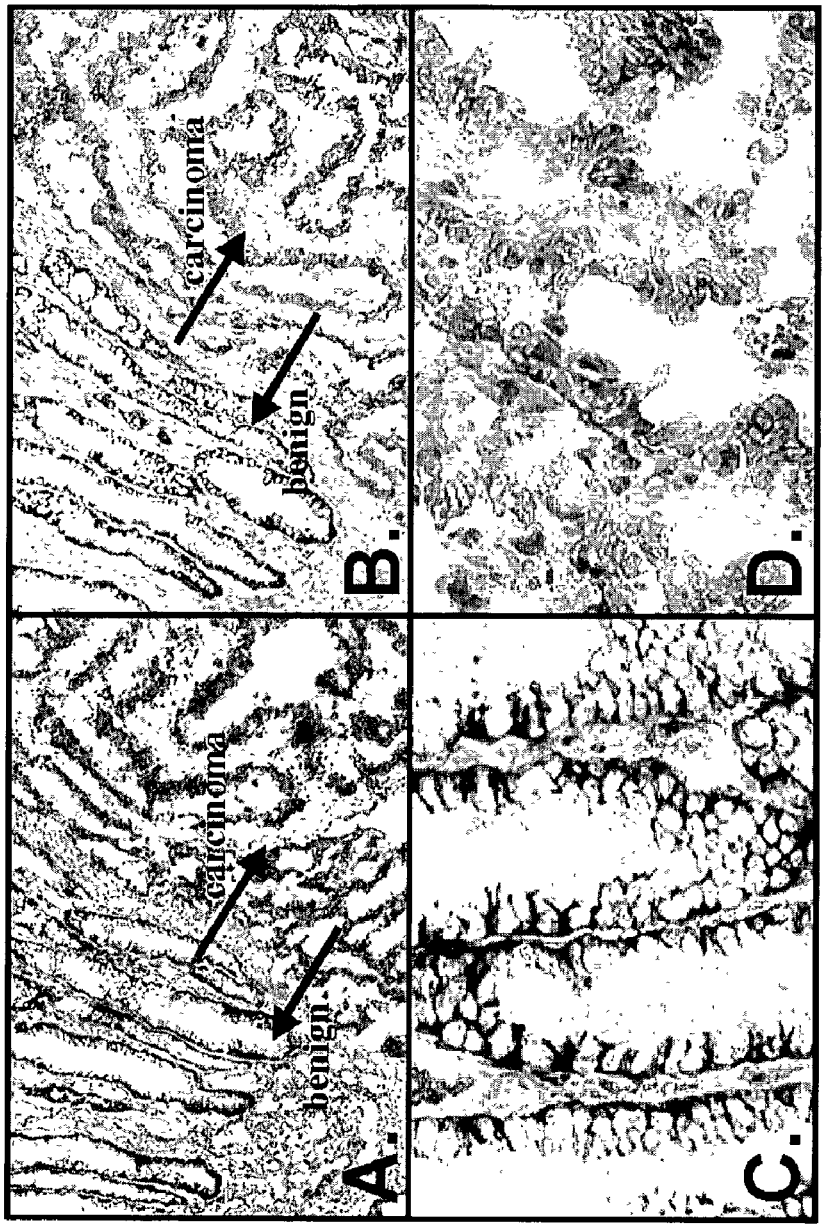
FIG. 8 shows changes in ERRP staining in the benign and the adjacent adenocarcinoma of the colon.

To evaluate the involvement of ERRP in epithelial tumors, we performed immunohistochemical staining to examine ERRP expression in colon and prostate tissues from patients containing benign and adjacent invasive adenocarcinomas. FIG. 8 shows changes in ERRP staining in the benign and the adjacent adenocarcinoma of the colon. FIG. 8-A shows hematoxylin and eosin-stained section of colonic mucosa containing an area of benign colonic epithelium ("benign") and adjacent invasive adenocarcinoma ("carcinoma"). Immunostain with polyclonal anti-ERRP antisera (1:2000 dilution) shows that the antibody stains the benign epithelium intensely but only weakly in the carcinoma (FIG. 8-B). Higher magnification of benign mucosa (FIG. 8-C) and invasive adenocarcinoma (FIG. 8-D) shows that ERRP localizes to the basolateral membranes in benign mucosa (the same localization as the bulk of EGFR) but loses that polarized distribution in invasive adenocarcinoma.

EXAMPLE 10

Figure 9:
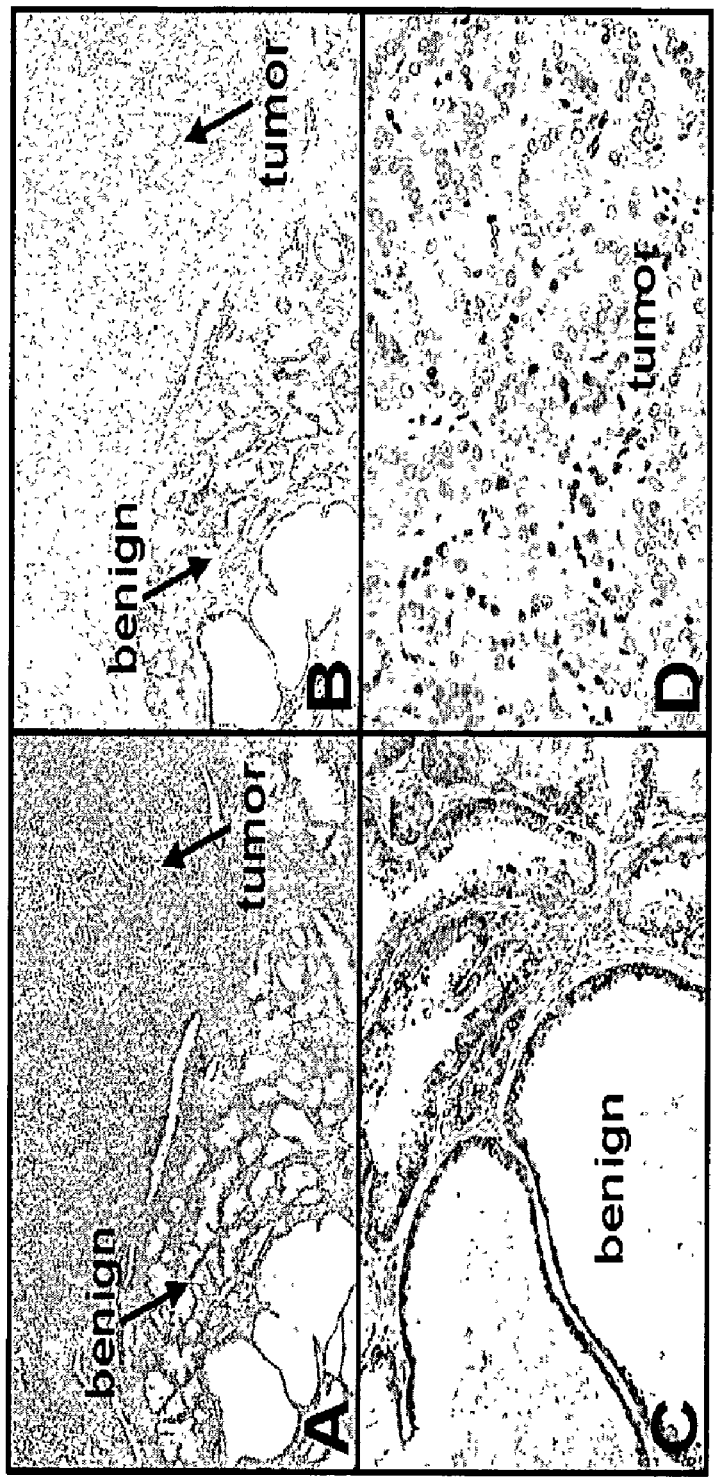
FIG. 9 shows changes in ERRP staining in the benign and the adjacent adenocarcinoma of the prostate.

We examined ERRP expression in the prostate tissue from a patient with well differentiated adenocarcinoma. FIG. 9-A shows hematoxylin and eosin-stained section of prostatic tissue containing an area of benign prostatic parenchyma ("benign") and a discreet nodule of invasive adenocarcinoma of the prostate ("tumor"). Immunostain with polyclonal anti-ERRP antisera (1:2000 dilution) shows that the antibody stains the benign epithelium intensely but only minimal staining of the tumor nodule is detected (FIG. 9-B). Furthermore, higher magnification of the anti-ERRP immunostain of benign prostatic glands shows that the antibody primarily reacts with the luminal aspect of the lining epithelial cells (FIG. 9-C). Higher magnification of the anti-ERRP immunostain of invasive adenocarcinoma shows a nonspecific faint immunoreactivity, and is primarily with luminal secretions (FIG. 9-D).

EXAMPLE 11

Figure 10:
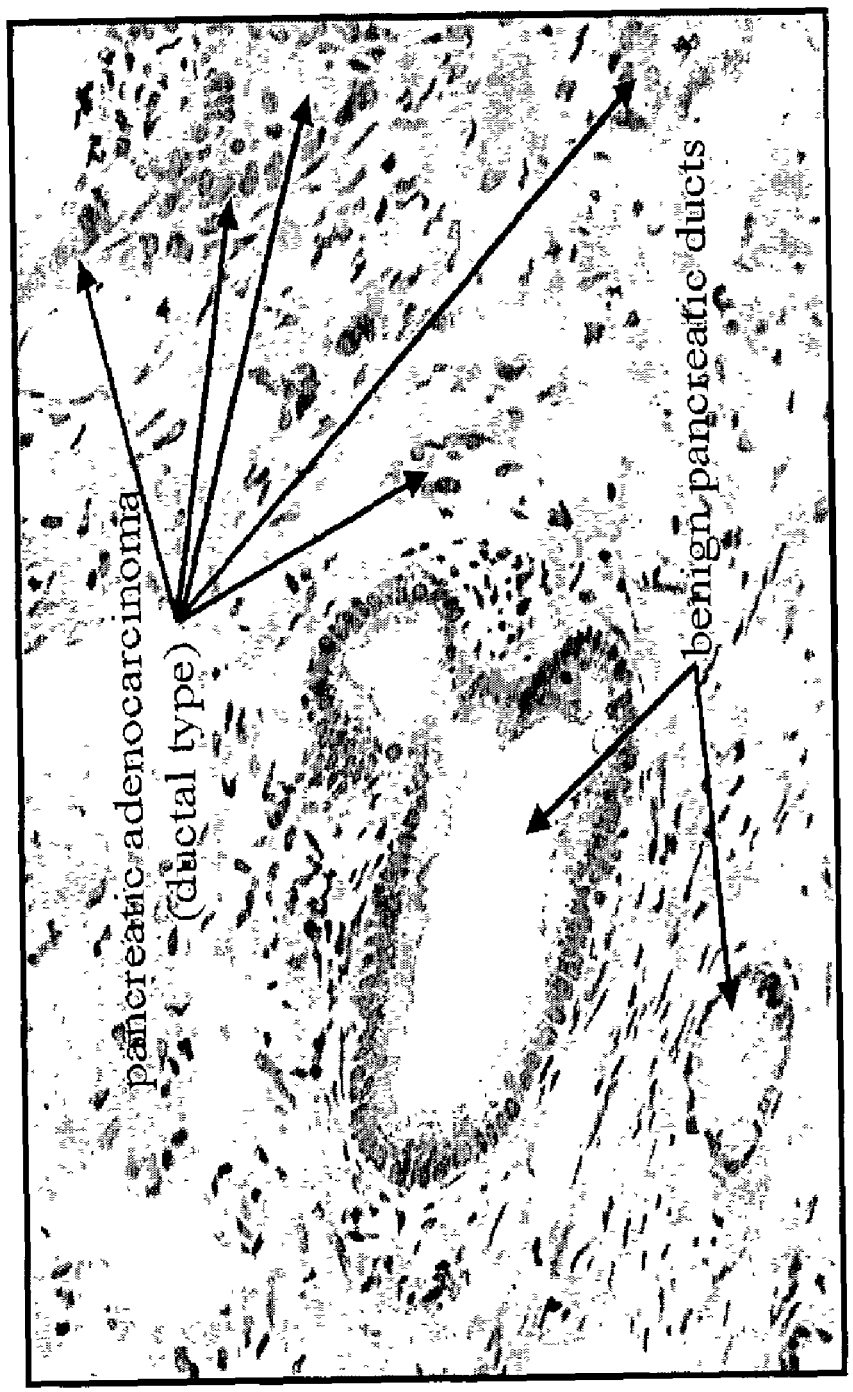
FIG. 10 shows ERRP expression in pancreatic tissue from a patient containing benign and invasive ductal cell adenocarcinoma.

We examined ERRP expression in pancreatic tissue from a patient containing benign and invasive ductal cell adenocarcinoma (FIG. 10). We observed that intense ERRP staining (1:1000 dilution) in the benign pancreatic ductal cells. In contrast, no ERRP immunoreactivity was observed in the region with adenocarcinoma (FIG. 10).

What is claimed is:

1. An antibody that specifically binds to the polypeptide of SEQ ID NO: 3.

2. The antibody of claim 1, wherein the antibody is monoclonal.

3. The antibody of claim 1, wherein the antibody is polyclonal.

4. An antibody that specifically binds to the polypeptide of SEQ ID NO: 4.

5. The antibody of claim 4, wherein the antibody is monoclonal.

6. The antibody of claim 4, wherein the antibody is polyclonal.

7. A method of making an antibody that specifically binds to the polypeptide of SEQ ID NO: 2 comprising providing the polypeptide of SEQ ID NO: 2;
injecting the polypeptide into an animal;
harvesting the animal's blood; and
purifying the antibody from the blood.

8. The method of claim 7 wherein the animal is selected from the group consisting of sheep, goats, mice, rabbits, and rats.

9. The method of claim 7 wherein the purifying step is accomplished by affinity separation.

10. A method of making an antibody that specifically binds to the polypeptide of SEQ ID NO: 3 comprising
providing the polypeptide of SEQ ID NO: 3;
injecting the polypeptide into an animal;
harvesting the animal's blood; and
purifying the antibody from the blood.

11. The method of claim 10 wherein the animal is selected from the group consisting of sheep, goats, mice, rabbits, and rats.

12. The method of claim 10 wherein the purifying step is accomplished by affinity separation.

13. A method of making an antibody that specifically binds to the polypeptide of SEQ ID NO: 4 comprising
providing the polypeptide of SEQ ID NO: 4;
injecting the polypeptide into an animal;
harvesting the animal's blood; and
purifying the antibody from the blood.

14. The method of claim 13, wherein the animal is selected from the group consisting of sheep, goats, mice, rabbits, and rats.

15. The method of claim 13, wherein the purifying step is accomplished by affinity separation.

* * * * *

SEQUENCE LISTING

<160> NUMBER OF SEQ ID NOS: 4

<210> SEQ ID NO 1
<211> LENGTH: 1958
<212> TYPE: DNA
<213> ORGANISM: Rattus norvegicus

<400> SEQUENCE: 1

```
gggtgtttta tttcctcctc ttcttcccgc actgtgcgct cctcctgggc tagggcgtct      60
ggatcgagtc ccggaggcta ccgcctccca gacagacgac gggtcacctg gacgcgagcc     120
tgtgtccggg tctcgtcgtt gccggcgcag tcactgggca caaccgtggg actccgtctg     180
tctcggatta atcccggaga gccagagcca acctctcccg gtcagagatg cgaccctcag     240
ggaccgcgag aaccacactg ctggtgctgc tgaccgcgct ctgcgcggca ggtggggcgt     300
tggaggaaaa gaaagtctgc caaggcacaa gtaacaggct cacccaactg ggcacttttg     360
aagaccactt tctgagcctg cagaggatgt acaacaactg tgaagtggtc cttgggaact     420
tggaaattac ctatgtgcaa aggaattacg acctttcctt cttaaaaacc atccaggagg     480
tggccggcta tttcctcatt gccctcaaca ccgtggagag aatcccttcg gaggacctgc     540
agatcatcag gggaaatgct ctttatgaaa acacctatgc cttagccatc ctgtccaact     600
atgggacaaa cagaactggg cttagggaac tgcccatgcg gaacttacag gaaatcctga     660
ttggtgctgt gcgattcagc aacaacccca tcctctgcaa tatggatact atccagtgga     720
gggacatcgt ccaaaacgtc tttatgagca acatgtcaat ggacttacag agccatccga     780
gcagttgccc caaatgtgat ccaagctgtc ccaatggaag ctgctgggga ggaggagagg     840
agaactgcca gaaattgacc aaaatcatct gtgcccagca atgttcccat cgctgtcgtg     900
gcaggtcccc cagtgactgc tgccacaacc aatgtgctgc ggggtgtaca gggccccaaa     960
agagtgactg tctggtctgc caaaagttcc aagatgaggc cacatgcaaa gacacctgcc    1020
caccactcat gctgtacaac cccaccacct atcagatgga tgtcaaccct gaagggaagt    1080
acagctttgg tgccacctgt gtgaagaact gcccccgaaa ctacgtggtg acagatcatg    1140
gctcatgtgt ccgagcctgt gggcctgact actacgaagt ggaagaagat ggcatccgca    1200
agtgtaaaaa atgtgatggg ccctgtcgca aagtttgtaa tggcataggc attggtgaat    1260
```

-continued

```
ttaaagacac actctccata aatgctacaa acatcaaaca cttcaaatac tgcactgcca      1320
tcagcgggga ccttcacatc ctgccagtgg cctttaaggg ggattctttc acgcgcactc      1380
ctcctctaga cccacgggaa ctagaaattc tcaagactgt gaaggaaata acagggtctt      1440
tgctgattca ggcttggcct gaaaactgga ctgacctcca tgcttttgag aacctagaaa      1500
taattcgtgg cagaacaaag caacatggtc agttttctct ggcggttgtc ggcctgaaca      1560
taacatcgct gccgtggcag gttccatcgc tgtcgtggca ggctgtgaca aggcccttgc      1620
accctctggc ccaaaataga gtcagctggg acactgggcc ctgaccttgt aagcttcctg      1680
taatgttagc ctgcccatgg cacccccaaca gcaagatcct gaagctcaag tttgatccta      1740
acaaaaccac cgctgctgcg gtttctggga gaagcaagca tttattcacc tgcaagatca      1800
catccctaac cttgactttg cttaagagtg ctgaatgaag atcctgtccc taaatcataa      1860
ctcaattctt ttgctcaagg aaaatgcact tgtcttcttc caaaaaaaaa aaatcaatat      1920
gcaaaatgga atttgaaata aaagcttttc taaaaatg                              1958
```

<210> SEQ ID NO 2
<211> LENGTH: 478
<212> TYPE: PRT
<213> ORGANISM: Rattus norvegicus

<400> SEQUENCE: 2

```
Met Arg Pro Ser Gly Thr Ala Arg Thr Thr Leu Leu Val Leu Leu Thr
 1               5                  10                  15

Ala Leu Cys Ala Ala Gly Gly Ala Leu Glu Glu Lys Lys Val Cys Gln
                20                  25                  30

Gly Thr Ser Asn Arg Leu Thr Gln Leu Gly Thr Phe Glu Asp His Phe
            35                  40                  45

Leu Ser Leu Gln Arg Met Tyr Asn Asn Cys Glu Val Val Leu Gly Asn
        50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Phe Leu Ile Ala Leu Asn Thr Val
                85                  90                  95

Glu Arg Ile Pro Ser Glu Asp Leu Gln Ile Ile Arg Gly Asn Ala Leu
           100                 105                 110

Tyr Glu Asn Thr Tyr Ala Leu Ala Ile Leu Ser Asn Tyr Gly Thr Asn
       115                 120                 125

Arg Thr Gly Leu Arg Glu Leu Pro Met Arg Asn Leu Gln Glu Ile Leu
   130                 135                 140

Ile Gly Ala Val Arg Phe Ser Asn Asn Pro Ile Leu Cys Asn Met Asp
145                 150                 155                 160

Thr Ile Gln Trp Arg Asp Ile Val Gln Asn Val Phe Met Ser Asn Met
               165                 170                 175

Ser Met Asp Leu Gln Ser His Pro Ser Ser Cys Pro Lys Cys Asp Pro
           180                 185                 190

Ser Cys Pro Asn Gly Ser Cys Trp Gly Gly Glu Asn Cys Gln
       195                 200                 205

Lys Leu Thr Lys Ile Ile Cys Ala Gln Gln Cys Ser His Arg Cys Arg
   210                 215                 220

Gly Arg Ser Pro Ser Asp Cys Cys His Asn Gln Cys Ala Ala Gly Cys
225                 230                 235                 240

Thr Gly Pro Gln Lys Ser Asp Cys Leu Val Cys Gln Lys Phe Gln Asp
```

-continued

```
                        245                 250                 255
Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
            275                 280                 285

Ala Thr Cys Val Lys Asn Cys Pro Arg Asn Tyr Val Val Thr Asp His
        290                 295                 300

Gly Ser Cys Val Arg Ala Cys Gly Pro Asp Tyr Tyr Glu Val Glu Glu
305                 310                 315                 320

Asp Gly Ile Arg Lys Cys Lys Cys Asp Gly Pro Cys Arg Lys Val
                325                 330                 335

Cys Asn Gly Ile Gly Ile Gly Glu Phe Lys Asp Thr Leu Ser Ile Asn
                340                 345                 350

Ala Thr Asn Ile Lys His Phe Lys Tyr Cys Thr Ala Ile Ser Gly Asp
                355                 360                 365

Leu His Ile Leu Pro Val Ala Phe Lys Gly Asp Ser Phe Thr Arg Thr
        370                 375                 380

Pro Pro Leu Asp Pro Arg Glu Leu Glu Ile Leu Lys Thr Val Lys Glu
385                 390                 395                 400

Ile Thr Gly Ser Leu Leu Ile Gln Ala Trp Pro Glu Asn Trp Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Gly Leu Asn Ile Thr Ser Leu
            435                 440                 445

Pro Trp Gln Val Pro Ser Leu Ser Trp Gln Ala Val Thr Arg Pro Leu
    450                 455                 460

His Pro Leu Ala Gln Asn Arg Val Ser Trp Asp Thr Gly Pro
465                 470                 475

<210> SEQ ID NO 3
<211> LENGTH: 27
<212> TYPE: PRT
<213> ORGANISM: Rattus norvegicus

<400> SEQUENCE: 3

Pro Trp Gly Val Pro Ser Leu Ser Trp Gln Ala Val Thr Arg Pro Leu
1               5                  10                  15

His Pro Leu Ala Gln Asn Arg Val Ser Trp Asp
            20                  25

<210> SEQ ID NO 4
<211> LENGTH: 15
<212> TYPE: PRT
<213> ORGANISM: Rattus norvegicus

<400> SEQUENCE: 4

Ala Val Thr Arg Pro Leu His Pro Leu Ala Gln Asn Arg Val Ser
1               5                  10                  15
```